US009078570B2

(12) United States Patent
Parks et al.

(10) Patent No.: US 9,078,570 B2
(45) Date of Patent: Jul. 14, 2015

(54) HIGH RESOLUTION SOLID STATE PRESSURE SENSOR (75) Inventors: Thomas R. Parks, Hermosa Beach, CA (US); Jae S. Son, Rancho Palos Verdes, CA (US)

(73) Assignee: Sierra Scientific Instruments, Inc.

( * ) Notice: Subject to any disclaimer, the term of this patent is extended or adjusted under 35 U.S.C. 154(b) by 1308 days.

(21) Appl. No.: 10/961,981

(22) Filed: Oct. 8, 2004

(65) Prior Publication Data
US 2005/0148884 A1 Jul. 7, 2005

Related U.S. Application Data (60) Provisional application No. 60/510,475, filed on Oct. 10, 2003.

(51) Int. Cl.
*A61B 5/02* (2006.01)
*A61B 5/03* (2006.01)

(52) U.S. Cl.
CPC ........................................ *A61B 5/037* (2013.01)

(58) Field of Classification Search
CPC ..................................................... A61B 5/037
USPC .................................. 600/485–488, 561, 587
See application file for complete search history.

(56) References Cited

U.S. PATENT DOCUMENTS

| 3,088,323 | A | * | 5/1963 | Welkowitz et al. | 73/727 |
| 3,750,476 | A | * | 8/1973 | Brown | 73/724 |
| 4,064,549 | A | * | 12/1977 | Cretzler | 361/283.1 |
| 4,064,550 | A | * | 12/1977 | Dias et al. | 361/283.4 |
| 4,114,606 | A | | 9/1978 | Seylar | 128/2.05 E |
| 4,278,092 | A | * | 7/1981 | Borsanyi et al. | 604/175 |
| 4,388,668 | A | * | 6/1983 | Bell et al. | 361/283.4 |
| 4,431,882 | A | * | 2/1984 | Frame | 200/5 A |
| 4,561,450 | A | * | 12/1985 | Bryant | 600/593 |
| 4,711,249 | A | * | 12/1987 | Brooks | 600/561 |
| 4,739,769 | A | | 4/1988 | Matthews et al. | 128/673 |
| 4,757,381 | A | | 7/1988 | Cooper | |
| 4,798,588 | A | | 1/1989 | Aillon | 604/122 |
| 4,809,709 | A | | 3/1989 | Brooks | 128/748 |
| 4,809,710 | A | | 3/1989 | Williamson | 128/748 |
| 4,815,471 | A | * | 3/1989 | Stobie | 600/488 |

(Continued)

FOREIGN PATENT DOCUMENTS

DE 2456980 6/1976
WO WO 02/064019 A 8/2002

OTHER PUBLICATIONS

Supplemental European Search Report, Application No. EP 04 81 6915, dated Jun. 30, 2009.

(Continued)

*Primary Examiner* — Rene Towa
(74) *Attorney, Agent, or Firm* — Wolf, Greenfield & Sacks, P.C.

(57) ABSTRACT

A pressure sensor and pressure-sensing catheter in which a deformable pressure sensing membrane is separated from an inner metalized surface on a rigid support by an air gap. An input allows a voltage to be applied to an electrode on the sensing membrane and an output allows reading of the signal modulation from the support surface. An outer sleeve overlays the membrane and a wire bus transmits the signals to a terminal connector. The catheter may include a vented air gap, a multiplexing wire bus, and an internal cable to maintain tension.

37 Claims, 9 Drawing Sheets

(56) References Cited

U.S. PATENT DOCUMENTS

| | | | |
|---|---|---|---|
| 4,815,472 A * | 3/1989 | Wise et al. | 600/488 |
| 4,873,990 A | 10/1989 | Holmes et al. | 128/748 |
| 4,887,610 A | 12/1989 | Mittal | 128/733 |
| 4,967,753 A * | 11/1990 | Haase et al. | 600/468 |
| 5,018,529 A * | 5/1991 | Tenerz et al. | 600/480 |
| 5,163,328 A * | 11/1992 | Holland et al. | 73/717 |
| 5,225,959 A * | 7/1993 | Stearns | 361/283.1 |
| 5,297,437 A | 3/1994 | Schneider | 73/705 |
| 5,450,853 A | 9/1995 | Hastings et al. | |
| 5,533,515 A * | 7/1996 | Coller et al. | 600/593 |
| 5,807,269 A | 9/1998 | Quinn | |
| 5,808,205 A * | 9/1998 | Romo | 73/718 |
| 5,836,894 A | 11/1998 | Sarvazyan | |
| 5,868,719 A * | 2/1999 | Tsukernik | 604/265 |
| 5,983,727 A | 11/1999 | Wellman et al. | |
| 5,987,995 A | 11/1999 | Sawatari et al. | 73/705 |
| 5,989,183 A | 11/1999 | Reisdorf | |
| 6,019,728 A * | 2/2000 | Iwata et al. | 600/486 |
| 6,051,293 A | 4/2000 | Weilandt | |
| 6,063,031 A | 5/2000 | Cundari et al. | 600/439 |
| 6,090,052 A * | 7/2000 | Akerfeldt et al. | 600/585 |
| 6,091,981 A | 7/2000 | Cundari et al. | 600/407 |
| 6,210,339 B1 * | 4/2001 | Kiepen et al. | 600/486 |
| 6,213,988 B1 | 4/2001 | McIvor | |
| 6,264,612 B1 * | 7/2001 | McConnell et al. | 600/486 |
| 6,394,986 B1 * | 5/2002 | Millar | 604/264 |
| 6,500,119 B1 | 12/2002 | West et al. | 600/437 |
| 6,511,478 B1 * | 1/2003 | Burnside et al. | 606/41 |
| 6,689,056 B1 | 2/2004 | Kilcoyne et al. | 600/300 |
| 6,824,521 B2 * | 11/2004 | Rich et al. | 600/561 |
| 7,020,525 B1 * | 3/2006 | Davis et al. | 607/36 |
| 2002/0130673 A1 | 9/2002 | Pelrine et al. | |
| 2002/0151816 A1 | 10/2002 | Rich et al. | |
| 2003/0078573 A1 | 4/2003 | Truckai et al. | |
| 2003/0079547 A1 * | 5/2003 | Baek | 73/716 |
| 2003/0097064 A1 * | 5/2003 | Talpade et al. | 600/434 |
| 2003/0105388 A1 | 6/2003 | Roy et al. | |
| 2003/0135120 A1 | 7/2003 | Parks et al. | |
| 2004/0068203 A1 * | 4/2004 | Gellman et al. | 600/587 |
| 2004/0082867 A1 * | 4/2004 | Esch et al. | 600/488 |

OTHER PUBLICATIONS

International Search Report, Application No. PCT/US04/33228, dated Mar. 21, 2007.

European Search Report related to EP 11 188 400, dated Jan. 18, 2012.

* cited by examiner

| 9A | 9B | 9C | 9D |
|---|---|---|---|
| Insert sheath in fixture | Pull Vacuum — Fasten sheath & dilate | Maintain Vacuum — Insert catheter | Release Vacuum — Shrink sheath & remove |

Circumferential

Sector  Spot

Flat Sided

HIGH RESOLUTION SOLID STATE PRESSURE SENSOR

CROSS-REFERENCE TO RELATED APPLICATION

This application claims the benefit under 35 USC Section 119(e) to commonly owned U.S. Provisional patent application Ser. No. 60/510,475, filed Oct. 10, 2003.

GOVERNMENT RIGHTS

The U.S. Government retains certain rights to this invention as provided by the terms of National Institute of Health grants 1 R43 DK56539-01 and 2R44 DK56539.

TECHNICAL FIELD

The present invention relates generally to pressure sensors and more specifically to a pressure sensor that may be adapted as a high resolution manometric catheter.

BACKGROUND OF THE INVENTION

The use of pressure measurements in small confined spaces is important in a number of different fields. In the field of diagnostic medicine and monitoring of patients, it is often necessary or useful to measure relatively small pressure changes inside various organs in the individual's body. A number of different devices have been constructed to measure these pressure changes. Such devices include pressure sensing catheters that may be used in coronary arteries, devices for use in the urethra, and esophageal pressure sensing instruments.

One example of a need to detect an internal organ pressure change is esophageal pressure analysis. The ability to detect and display pressure differences over time provides a tool for manometric analysis both in the esophagus and potentially other parts of the gastrointestinal tract such as the stomach, duodenum, small bowel, colon, and anorectum.

Gastrointestinal motility disorders remain significant both in terms of the number of patients having symptoms of these disorders and the health care resources required to treat these disorders. Imaging methods (including endoscopy and radiography) provide some information regarding gastrointestinal organ structure and the movement of contents within these organs. Other imaging techniques are limited to diagnosis of disorders only if the disorder is characterized by a change to the organ's appearance or conspicuous abnormalities in the movement of the contents within such organs. However if the gastrointestinal disorder is simply an abnormality in the contracting function of the organ, an alternative diagnostic method is required. Manometry provides a sensitive measure of pressure change within an elongate organ, allowing additional useful information for diagnosis, treatment or monitoring of a disorder.

A number of different devices to measure pressure (specifically within human organs) have been disclosed. For example, U.S. Pat. No. 4,887,610 discloses a manometric catheter that includes a sleeve segment having two attached metal electrodes. This design allows the simultaneous measurement from a single location of pressure and electrical events specifically in human sphincters.

U.S. Pat. No. 4,873,990 discloses a probe for measuring circumferential pressures in a body cavity. This reference discloses the measurement of urodynamic pressure for evaluating human urinary sphincter function. Along the length of the probe are a number of deformable wall sensors. These wall sensors have flexible sidewall areas and a means to modulate the signal as the wall of the probe moves under the influence of external pressure.

U.S. Pat. No. 4,739,769 discloses a pressure transducer in which a fluid circulated through a tube at a constant flow rate expands into a bubble in a catheter. Absent an external pressure a bubble expands where there is no increase in the flow resistance to the system.

U.S. Pat. No. 5,987,995 discloses a fiberoptic pressure catheter including a light source, an optical fiber coupled to receive light from the light source and the sensor head that is optically coupled to the optical fiber. The housing has an opening that is enclosed by a membrane. The membrane may move in response to pressure differences between the membrane chamber and the pressure outside a sensor head. A resilient ribbon is coupled to the chamber such that it may move in front of the optical fiber. The ribbon is also coupled to the membrane such that it is repositioned by the membrane in response to pressure changes, thereby reflecting varying amounts of light back into the optical fiber based on the amount of pressure on the membrane.

U.S. Pat. No. 5,983,727 discloses a plurality of membranes including an incompressible mount and a deformable membrane mounted over the mount such that there is a cavity between said membrane and mount surface. A non-contact transducer within the mount detects deflection of the membrane.

U.S. Patent Application Ser. No. 60/343,714, also owned by the present applicant, discloses various methods and algorithms for visualization of values, including internal pressure measurement. Such visualization includes display in a number of formats of pressure readings.

All of the above references are hereby incorporated by reference for all purposes herein.

There are a number of limitations of the prior art. These include the inability to provide sufficient number of solid state sensors in a sufficiently small diameter tool to allow for a pressure sensor that is able to reliably resolve the spatial characteristics of pressure waves in elongate organs. The pressure sensing catheters currently available with a higher number of pressure sensors are of the water-perfused pneumohydraulic designs. These designs are not solid state, tend to be cumbersome and expensive, and are technically challenging to use. One drawback of such designs is that to overcome gravity effects, the patient must remain supine to ensure that the external transducers are at the level of the esophagus. In addition, sterilization of these catheters is difficult.

In addition, while a sufficient number of sensor sites has been achieved using perfussed water technology, these sensor sites have highly localized "spot" sensitivity and hence render unreliable measurements in regions of physiological asymmetry such as the pharynx and the upper esophageal sphincter. The use of circumferential sensing yields reliable measurements in these regions.

In addition providing a robust, easily sterilizable and simpler to manufacture device is needed.

DETAILED DESCRIPTION OF THE INVENTION

The present invention generally may be viewed as including a few broad concepts which the present examples illustrate. The first broad concept is the connection of solid state pressure sensors each having an input and an output. The output signal is modulated indicating pressure within the sensing area. The inputs and outputs are electrically connected to a bus such that multiple sensors share a single input line and multiple sensors share an output line (i.e. an electrically conductive path). In using such a configuration the number of lines required in a device may be reduced. This allows a smaller diameter catheter with a larger number of more closely spaced pressure sensors. With such a configuration, the ability to spatially resolve pressure changes, such as contractions as they move through an organ (e.g. peristalsis) is possible.

A second concept of the invention is the use of spaced air gap pressure sensors in a pressure sensing catheter. The use of such pressure sensors, rather than a liquid pressure sensor, provides a number of advantages such as increased reliability, reduced maintenance requirements and simplicity of operation. Such a solid state device also enables a robust system that produces repeatable results.

A third aspect of the present invention is the use of an axially rigid central cable to provide a flexible assembly that has high axial rigidity. These results and other advantages are illustrated in the following examples.

A fourth concept of the invention is the use of a deformable pressure sensing membrane mounted on a rigid structure having a coaxial electrode surface, the pressure sensing membrane mounted such that the side edges of the membrane are fixed to the rigid structure, flanking an inner facing membrane electrode. These flanking sections may be attached to the rigid structure. This allows the pressure sensor to shunt-axial or bending loads.

A fifth concept of the invention is a pressure sensing catheter including a number of pressure sensors, each having an input and output, with the inputs and outputs connected to a flexible ribbon cable.

A sixth concept of the invention is a pressure sensor or pressure sensing catheter in which pressure is transduced using a deformable membrane that is coaxial with an inner metalized surface, wherein the membrane and surface are separated by a gap. The gap is in communication with an interior volume such that a gas in the air gap can move from the area between the deformable membrane and metalized surface, into the interior of the rigid structure having the metalized surface to allow the gap to be vented to a selected pressure condition, such as ambient air or a controlled pressure chamber. If the capactive pressure sensor is included in a catheter, the catheter may have a venting tube to vent to ambient air or to a pressure chamber.

A seventh concept of the invention is use of an outer biocompatible covering extending over a plurality of solid state pressure sensors. Such a biocompatible covering may be a disposable sheath, a outer compliant sleeve, or both.

An eighth concept of the invention is a deformable membrane pressure sensor in which the deformable membrane includes a plurality of slits that allow deformation of the pressure sensing membrane toward a coaxial inner conductive surface, narrowing an air gap that separates the deformable membrane from an inner surface.

A ninth concept of the invention is a capacitive pressure sensor that includes a deformable membrane that has a plurality of traces on the membrane. One trace is joined to an outer electrode on the membrane, a second allows connection to an inner electrode on a rigid substrate, and a third may be used to ground the rigid substrate and membrane to isolate the pressure sensor from ambient dielectric interference.

A tenth concept of the invention is a capacitive sensor having a rigid structure and a deformable membrane mounted on the rigid structure such that an air gap is formed between an inward facing electrode on the deformable membrane and a metalized electrode surface on said rigid structure. A raised rib on said rigid structure allows positioning of the deformable membrane such that the electrode on the deformable surface is separated from the electrode on the rigid structure by a selected distance.

Another concept of the invention is a capacitive pressure sensing catheter which includes a metal rigid solid support and an overlaying deformable membrane, the support and/or the membrane grounded to make the structure insensitive to ambient dielectric changes.

Effective representation of gastrointestinal and other motor events may be dramatically improved by increasing the number of pressure sensors to allow for sufficient number of sensors to visualize pressure changes along the entire relevant length. But this must be done with a device that still is sufficiently small in diameter to be tolerated in intubation. The various features of the present invention allow from this improvement.

Circumferential sensing as provided by one embodiment of the present invention allows accurate sensing in regions of asymmetry of physiological pressure such as the oropharynxs and upper esophageal sphincter. Technologies that provide only "spot" sensing at one point or region on the catheter surface give highly variable readings depending on where the sensitive region is oriented relative to the asymmetry. The operator typically has no control over this orientation and so the measurements can be unreliable. Circumferential sensing also maximizes the available capacitive electrode area (the conductive surface area on each side of the air gap) and thereby maximizes the capacitive signal (increased signal to noise ratio).

Figure 1:
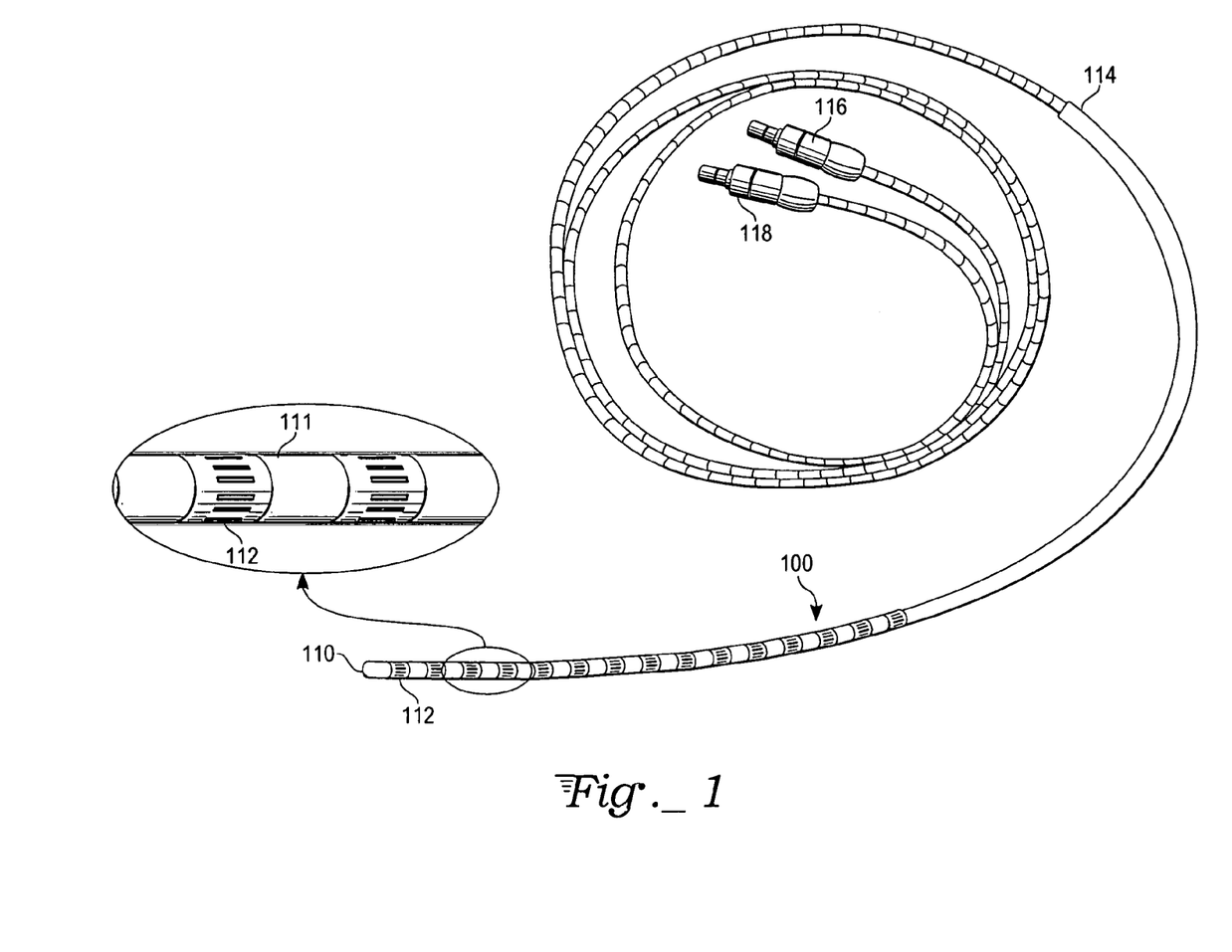
FIG. 1 is a perspective view of a pressure sensing catheter.

With respect to FIG. 1 a catheter 100 includes a longitudinally extending non-rigid outer tube 114 which forms the outer surface of the catheter. Tube 114 may be a silicone sleeve that is 0.050 to 0.001 inch thick. This material is biocompatible and should not degrade or substantially deform under the conditions within the organ in which the device is used. A material which has been certified and approved for use in implantable devices and has sufficiently high moisture barrier and mechanical compliance properties should be acceptable in this respect. In addition, physiological compatibility is enhanced by incorporating an internal structure to make the device axially rigid, as will be described herein.

As used herein, sleeve refers to a permanent structure overlaying the pressure sensors. This may be frictionally fit over the pressure sensors. If a sleeve is used alone, it must be sterilized between each use. A sheath is a thin disposable structure that may be fit onto a catheter. Such a device would be sterile, and the catheter could be simply inserted into a sheath prior to use, eliminating further need for sterilization of the device. Either a sleeve or a sheath may be used with a catheter, and preferably both a sleeve and a sheath are used.

The process of disinfecting manometric catheters presents certain difficulties both to a manufacturer and the user of these catheters. For perfused water pressure sensors, small water flow holes are often blocked by material present within an elongated internal organ (such as mucus in esophageal measurements). Such material, if not removed from the catheter immediately, hardens and might permanently damage the device or preclude complete disinfection. Sterilization (as by autoclave) is satisfactory for disinfection or sterilization of such a device but is time consuming. Also, the high pressure and temperature of an autoclave sterilization is not generally adaptable for sterilization of solid state devices.

The solid state catheter shown in FIG. 1 is easier to disinfect using chemical agents than perfused water designs. However, such chemical disinfection must be compatible with the outer sleeve without degrading the sleeve material.

To avoid the degradation of the outer catheter sleeve (which may degrade when typical disinfectants are used) one approach is to use organic soap to remove any protein before using a suitable disinfectant. However this adds an additional time-consuming step to the disinfection process. An alternative is to simply use a sanitary disposable sheath, either alone or on top of a outer sleeve.

In one embodiment shown in FIG. 1, the outer sleeve is a one-quarter millimeter thick tube of silicone. Molded end 110 does not contain internal sensors. As such, end 110 may be a solid silicone section of a narrower diameter that abuts the terminal sensor in the internal lumen of the sleeve.

In some embodiments the catheter may be inserted into a sheath. Such a sheath may include a custom design string balloon. The sheath may be manufactured as a prepackaged component in a pre-sterilized enclosure with an insertion stick inside the sheath.

FIGS. 9A-9D show one insertion methodology of a sheath onto a catheter. The sheath is introduced into a tube that is slightly larger than the diameter of the sheath. A proximal end of the sheath is folded back against the tube to form a seal. The tube is then attached to a vacuum source that evacuates the space between the tube and the sheath causing the sheath to expand. The insertion stick is removed and the pressure sensors mounted on a cable are introduced into the sheath. The vacuum is then released and the sheath contracts over the catheter. The catheter is then ready for calibration and clinical use. To remove the sheath, the sheath is again sealed on the vacuum fixture and vacuum is again applied. This process is illustrated in FIGS. 9A-9D.

In another embodiment shown in FIGS. 10A-10D, an alternative sheath insertion method is shown. In this embodiment the sheath is an extremely thin material (for example a thickness of 0.001 inch or less). The sleeve has a "baggy" or loose fit over the pressure sensors. It is preferred that the sheath be as thin as possible to both minimize the effect on the pressure measurements and to reduce patient discomfort. Given that the tissues of the sinuses and the throat are very sensitive to irregularities, a thinner, softer material that provides a more compliant surface is preferred. On the interior of the sheath a lubricant (e.g. talc, cornstarch, or a very light oil or silica lubricant) may be used to ensure that the catheter does not stick to the sheath during insertion or removal.

Figures 10A, 10B:
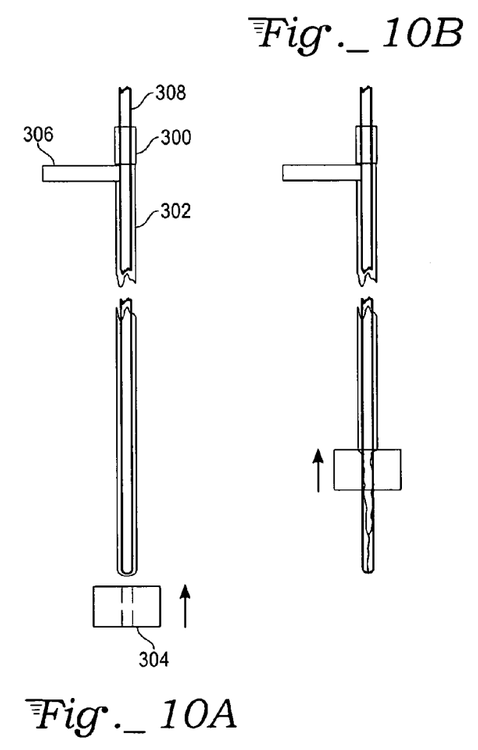
FIGS. 10A-10D are front views showing an alternative process of assembling an outer sheath onto the pressure sensors.

With reference to FIG. 10A, a rigid collar 300 is attached to the open end of the sheath 302. This gives a user a rigid structure to grip during insertion.

During insertion, a sliding ring 304 is slid over the sheath. The sliding ring may be made of a relatively soft foam rubber such that it is able to slightly deform. It is sized to be a relatively tight fit over the circumference of the catheter. As shown in FIG. 10B, the ring forces the air in the sheath out the open end as it moves up the catheter. It is important to remove this air between the sheath and the sensors because this can cause errors in pressure measurement (e.g. the peristaltic action of the esophagus can drive the air in a distal direction.) In addition, an air bubble that extends over multiple sensors can cause an equal pressure indication from those multiple sensors despite the fact that the physiological pressures at the corresponding locations are not the same.

Figures 10C, 10D:
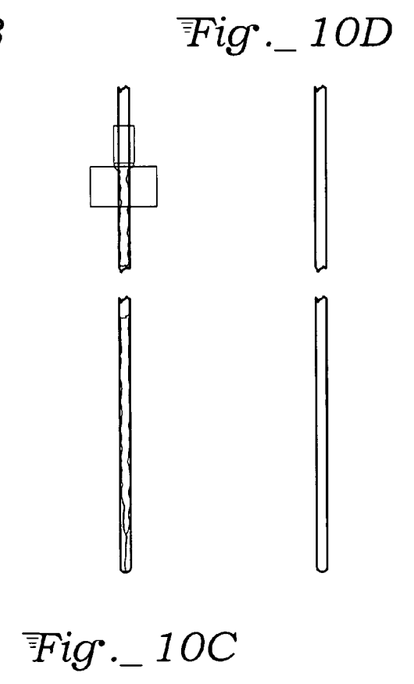

In FIG. 10C, once the sliding ring 304 is at the top of the sheath 302, the closure 306 may be tightened to secure the sheath over the pressure sensors, preventing any additional air from entering the sheath. Elastic adhesive tape may be used for such a closure.

Figure 11A:
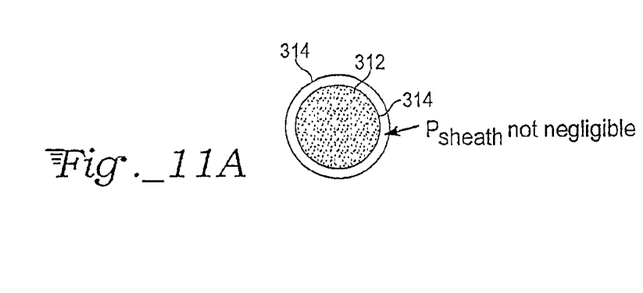
FIGS. 11A, 11B are cross sectional views of a pressure sensor and outer sleeve having a trapped air bubble completely separating the outer sleeve from the pressure sensing membrane and having the trapped air removed, respectively.
Figure 11B:
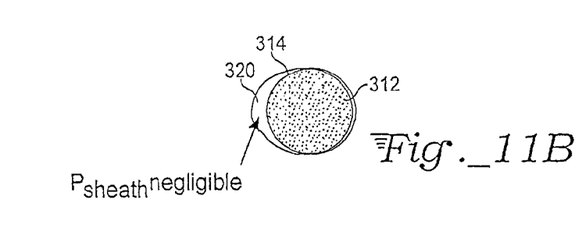

This design tolerates some remaining air in the sheath. A large air bubble trapped over the sensors could change the reading of a sensor only if the space between the sheath and the sensor were fully inflated. The pressure measured by a sensor $P_s$ is determined by the formula $P_S = P_{sh} + P_{ph}$ where $P_{sh}$ is the pressure gradient across the sheath from inside to outside and $P_{ph}$ is the physiological pressure to be measured inside of an organ. Because the sheath acts as a thin membrane, $P_{sh}$ is negligible unless the air fully inflates the sheath membrane in this area. Thus as shown in 11b, where outer sheath 314, overlays sensor 312 such that air gap 320 does not extend around the sensor, the effect is negligible. In the case of 11a, the bubble 312 does completely inflate the sheath resulting in error.

The design of this embodiment includes a reservoir volume, lying between the outer diameter of the catheter and the inner diameter of the sheath, which may contain small air pockets without affecting the sensed pressure. The mitigates two adverse conditions: 1. Pressure measurement errors noted above, and 2. Bubbles spanning multiple sensors (as described in relation to the insertion of the membrane.) The second instance would only occur if enough air were introduced into the outer sleeve to fully inflate the area between at least two sensors.

Figure 12A:
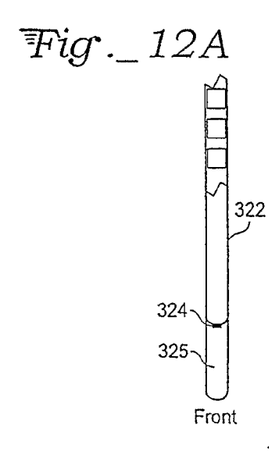
FIGS. 12A, 12C, and 12E are front views of a pressure sensor having an outer sleeve that includes a reservoir tip, shown before during and after intubation.
Figures 12B, 12C:
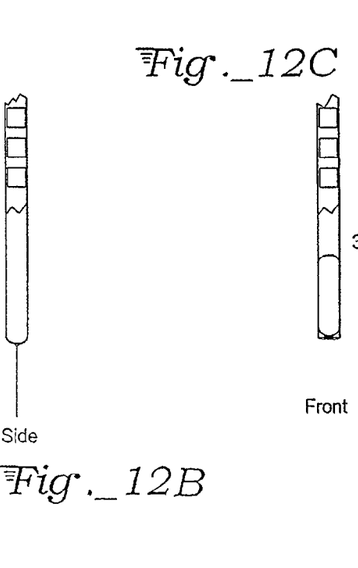
FIGS. 12B, 12D, and 12F are side views of a pressure sensor having an outer sleeve that includes a reservoir tip, shown before during and after intubation.
Figure 12D:
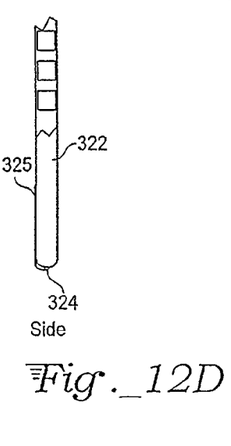
Figure 12E:
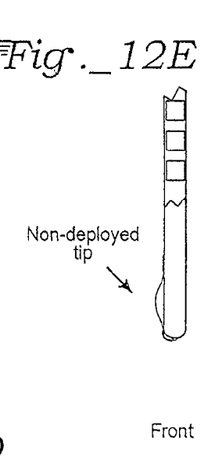
Figure 12F:
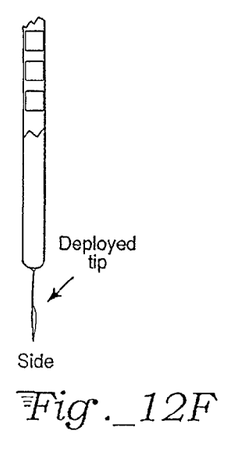

In FIGS. 12A, 12B, the sheath 322 is shown having a reservoir 325 at the end of the sheath 322. A welded, bonded or otherwise affixed plastic stop 324 limits insertion of the catheter, but allows the air bubble to pass into a distal reservoir via openings on the sides of plastic stop 324. In FIGS. 12C, 12D, the reservoir tip 325 is shown folded along the side of the body of the device during insertion of the catheter into the patient. After intubation, the tip deploys (e.g. into the stomach) and provides a reservoir for remaining air, as seen in FIGS. 12E, 12F. The peristaltic pressure within the organ into which the device is inserted may act to pump air from about the sensors into the tip.

Returning to FIG. 1, within outer sleeve 114 is pressure sensors 112. As noted below in relation to FIGS. 13A-13E, the pressure sensors may be circumferential, sector pressure sensors, spot pressure sensors, or have other designs. These sensors are spaced at intervals extending back from tip 110. In the illustrated embodiment, thirty-six pressure sensors are used. Each of the pressure sensors has an input and an output. The input is connected to an input wire that provides a voltage signal to the sensor. These input wires are terminated at terminal connector 116. The terminal connector has pin, pads, or other means for connecting this device to a voltage source. Similarly an output from each sensor is attached to an output wire extending through the sensors through sleeve 114 and to terminal connector 118. Again each line (wire) may terminate at a pin, pad or other contact that allows it to be joined to an electronic device to analyze the modulation of the voltage from each sensor. While it is contemplated that any voltage modulating pressure sensor may be used, it is preferred to use capacitive sensors in which the capacitance of a sensor membrane is modulated by pressure changes. This will be described in relation to the remaining figures, which use a circumferential air gap configuration as an example.

With the design of FIG. 1, the device has pressure sensors that extend to the sphincter at the entrance to the stomach. When inserted the distal tip 110 extends into the stomach. The sensors are able to provide a real time measurement of pressure distribution (including quasi static sphincter pressure and peristaltic pressure waves as they propagate through the gastrointestinal tract. As shown in FIG. 1, no sheath is used.

As shown in FIG. 1, the space between sensors 122 is filled with a flexible material (e.g. silicon) and the outer sleeve 114 is supported by this material and the sensors 112. An internal flex harness provides axial stiffness.

Figure 2:
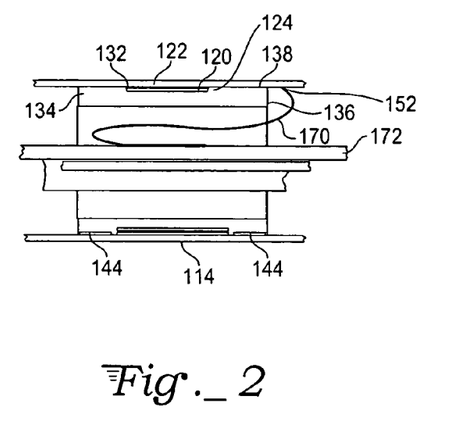
FIG. 2 is a side cross-section of an air gap pressure sensor.

With reference to FIG. 2, a cross-section through a pressure sensor is shown. A biocompatible outer sleeve 114 is the longitudinally extending non-rigid tube providing the outer surface of this device. It is relatively thin-walled (for example, one quarter of a millimeter thick) and biocompatible such that the device may be introduced into an internal organ of a patient. Biocompatibility is only one of the desired of the sleeve. It also should have good mechanical properties (low compression set (i.e. returns to its original shape after being compressed or stretched)) to minimize hysteresis in the pressure signal characteristic. Also for the capacitance sensing embodiment is should have very low moisture and water vapor permeability. This is because changes in humidity in the air gap will cause changes in dielectric constant of the air and hence erroneous changes in indicated pressure. It has been found that the described embodiments, including one mm thick silicon sleeves, work well. The sheath may be a thermal plastic elastomer to enhance moisture impermeability.

A precision-turned sensor support tube 126 forms a support structure for the pressure sensor. Such an element may be a metal "spool" which is mass-producible. A plurality of ridges 134, 132, 138, 136 extend from the outer surface of spool 126. Such ridges are annular raised structures on the surface of spool 126. Overlying these ridges is a sensing membrane 122. Epoxy strips 144 are positioned between ridges 134 and 132, and ridges 138 and 136, respectively. These epoxy strips may be precision die cut strips that allow the sensing membrane 122 to be firmly secured to spool 126 at a known height above surface 124. This height is precisely controlled by the height of the adjacent ridges of the spool. Between ridges 132 and 138 no epoxy strip is inserted. Thus there is an air gap between the sensing membrane 122 and the inner surface 124 on spool 126.

Sensing membrane 122 may be a precision laser cut membrane with a thin metalized coating that has been etched to form an appropriate electrode pattern. Vacuum metal deposition may be used to metalize a central sensing portion on the spool which is electrically connected to an output on the membrane. A thin dielectric coating on surface 124 of the spool and underlying the vacuum deposited metal portion may be used to electrically isolate the spool from the latter electrode. These two nominally parallel, coaxial surfaces, separated by an air gap thus become a capacitive sensing means. The spool is one example of the rigid support structure that may be used for such a capacitive sensor.

Figure 2A:
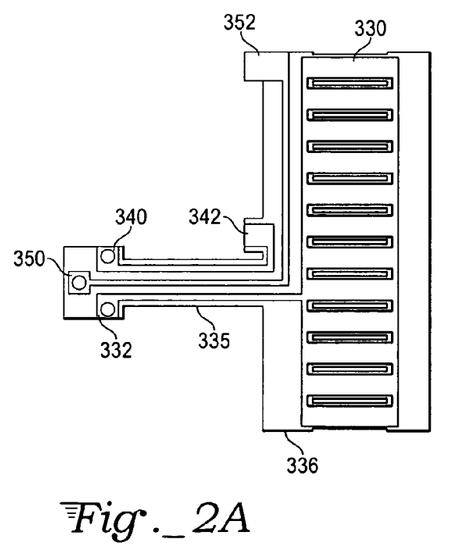
FIG. 2A is a bottom (inside surface) view of the sensing membrane before assembly onto a rigid tube.

With reference to FIG. 2A, a flattened membrane is shown. This membrane may be affixed over the spool by epoxy spacers to secure the sensing membrane into a fixed place. In FIG. 2A, the membrane is a very thin material, such as 0.001 inch thick polyimide. Coated onto this material is a thin 0.2 micron copper pattern. Polyimide is preferred for its mechanical properties (e.g. low compression set, low hysteresis, etc.). Thicker copper would result in metal yield effects under pressure during deformation, increasing hysteresis. The copper is initially fully plated onto one side of the membrane and then is precision etched into a pattern using standard photo lithograph methods.

Figure 2B:
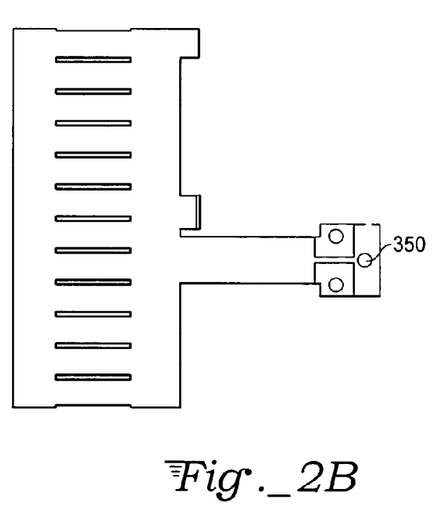
FIG. 2B is a top (outside surface) view of the sensing membrane before assembly onto a rigid tube.

On the inside face, a current is introduced in input 332, providing an AC voltage to strip 330. A ground 350 is in electrical communication to interconnect tab 352, which is connected to the spool for electrical shielding. Electrode 340 is the output electrode and is connected to tab 342, which is interconnected to the metalized area on the spool. After bonding to a spool input 332, output 340 and ground 350 extend on arm 335 from the side of the sensor, allowing connection to wires or lines for remote connection to the sensor input and output. Preferably ground 350 extends to outside the membrane, as seen in 2B, to shield the outside of the sensor from ambient dielectric changes. Arm 335 may extend to a wire bus for connection of the output and input from a sensor to the wire bus.

Figure 3:
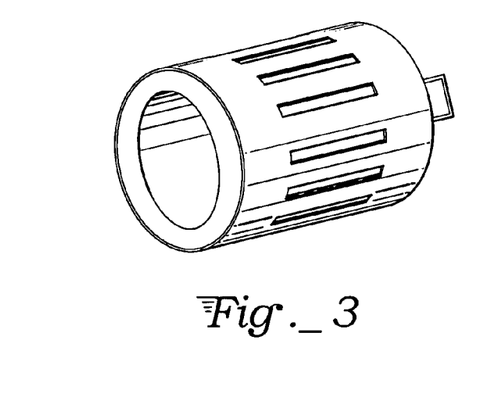
FIG. 3 is a side perspective view of an air gap pressure sensor.

With reference to FIG. 3, the perspective view of the device shows sensing membrane 122 overlying spool 126. A central strip on sensing membrane 122 has longitudinally oriented slits 150 which extend entirely through the sensing membrane 132. When the outer sleeve is positioned over the sensing membrane, pressure from the circumferential area surrounding the outer sleeve is transferred to the sensing membrane which then is able to deform slightly and press into the gap towards the inner surface shown in FIG. 2.

The present design of a flexible membrane secured over a rigid substrate has a number of useful features. One is the distribution of axial load. Some forces will stress the sensor, including axial pressure from bends in the catheter as the catheter is positioned inside an elongate organ. The deformable area of the membrane and the associated metalized electrode surface on the deformable membrane are flanked on each side by an attachment region that are secured to the rigid support (e.g. spool). These non-sensing areas minimize the axial stress forces bearing on the pressure sensing membrane, reducing error.

Tab 152 extends from the side of sensing membrane 122. In practice 1, 2, 3 or more tabs may be used, which extend beyond spool 126. On the underside of tab 152 are integral electrical interconnections. With reference to FIG. 8B, sensing membrane 122 is electrically linked to an input pad 160, a ground 164, and an output 162. Input 160 has a voltage to be introduced into the device and onto the sensing membrane. Preferably this voltage is an alternating current (AC) signal. In one embodiment, the AC signal has a frequency below 250 kHz.

With reference to FIG. 2 when a pressure is introduced against the biocompatible outer sleeve 114, this is transferred to the sensing membrane 122. The slits 150 shown in FIGS. 3, 8B allow membrane 122 to deflect towards inner surface 124 reducing the height of the air gap to a significantly greater degree than would occur if the membrane were continuous (i.e. without slits). This enables a greater increase in the capacitance of the capacitor effected by the membrane and spool electrodes and hence yields greater pressure sensitivity. This change in capacitance causes modulation of signal at output 162. Both the input 160, and the output 162 are joined to input and output lines (wires) as described below.

The change in voltage is read from the output wires at a terminal end by an electronic device that is not part of the catheter. The catheter may be linked to this device by electronic couplers as previously described. The conversion of the voltage modulation into a pressure reading may be done:
1. By a formula relating the change in voltage to a change in the gap between the electrodes, which correlates to the pressure of the device.
2. Calibration of the catheter. The sensing portion of the catheter may be inserted into a sealed chamber and subjected to pressure changes as the voltage modulation is measured. Individual sensors may be isolated into individual, pressure regulated compartments, or the catheter as a whole may be subject to a pressure variation.

Returning to FIG. 2, extending from sensing membrane 122 is tab 152. The inputs and outputs are connected to lines or wires in harness 170 which is joined to shielded cable 172. This is transferred by shielded cable 172 to the terminal connectors. As shown in FIG. 1 the terminal end of this cable allows connection to electronic circuitry to determine the modulation in voltage and hence the applied pressure at the membrane.

One important feature of this particular embodiment is the minimization of the coupling of the bending and/or tensile stresses to the sensor. The use of a rigid support spool with annular ridges and epoxy strips to firmly secure the sensing membrane onto the spool on both axial sides of the free-deflecting length of the membrane, provides a very rigid structure which is minimally affected by bending and tensile loads. The bending and tensile loads are shunted to the rigid spool and thus the strain from these forces detected by the sensing membrane is very small.

A second design issue is mitigating the hysteresis effects in the applied pressure versus modulated voltage characteristic, for example, those resulting from pressure deflection elements. This may be in part effected through selection of materials and thickness of both outer sleeve and membrane. It has been found that a thermal plastic elastomer in a thickness of ten thousandths of an inch provides sufficient environmental protection to the sensors and has sufficiently low compression set to have minimal hysteresis effect on the transducing mechanism. It has been found also that a one thousandth of an inch thick polyimide membrane and an air gap of four thousandths of an inch resulted in relatively low hysteresis under both low pressure and full range pressure cycling conditions. In addition, in conjunction with the aforementioned slits in the membrane, this configuration provided a high output signal.

Figure 6:
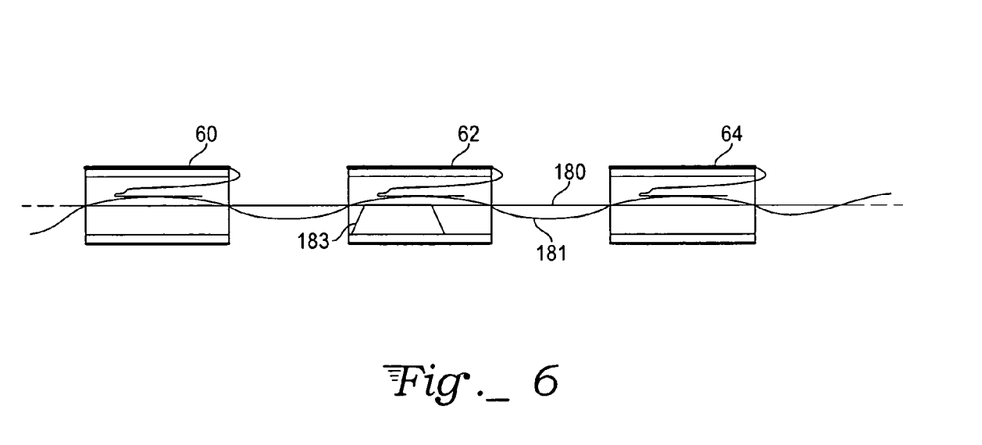
FIG. 6 is a side cross-section showing three sensors.

With reference to FIG. 6 a plurality of sensors without the outer sleeve are illustrated. In FIG. 6 pressure sensors 60, 62, 64 are part of a single pressure sensing device. An axial stress bearing cable 180 is positioned such that it extends through an interior area of each of the rigid spools of sensors 60, 62, 64. Component 180 may function as a safety leash that extends coaxially through the pressure sensors in the catheter. This cable-like element is flexible and may be bent, but is rigid in tension so that the sensing section cannot stretch. This cable also is sufficiently rugged that it may be used to bear a load without fatigue-related degradation as the catheter is extended into and out of an elongate organ. The signal bearing components (i.e. the sensor elements, the flex harness (electrical bus element) and the interconnections) are not subject then to the stresses of the axial loads (primarily due to design of the sensor, with the sensing membrane flanked by supporting regions of membrane on either side affixed to the rigid substrate) and hence the assembly is more reliable. Optionally a structure 183 may be linked to the axial stress bearing cable 180, although this may not be needed. It should be realized that the flexible outer sleeve, not shown in FIG. 6, extends between the pressure sensing components. This space may be filled with silicone rubber that is molded to have the same cylindrical cross-section as the sensor elements so that the assembly has a continuous outer diameter. Thus these areas between the components are less rigid and allow the catheter to bend as necessary to accommodate the shape of the internal organ into which the catheter is inserted. The input and output signals may be transferred to the sensing membranes from the signal bearing component.

Figure 8A:
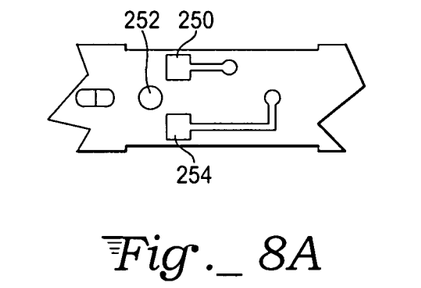
FIG. 8A is a top view of the flex harness showing the electrical pads.
Figure 8B:
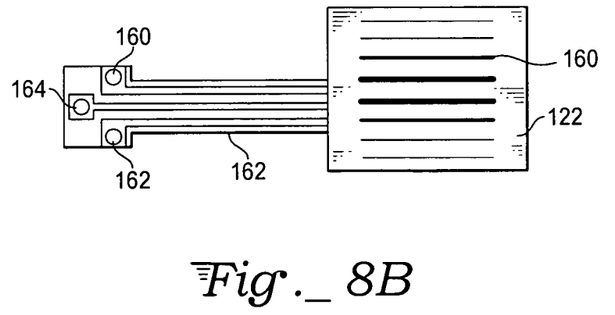
FIG. 8B is a top view showing the electrical pads of a pressure sensor.

FIG. 8A illustrates the electrical pads on the flexible harness, which is transmitted to the shielded wire cable. The input 250 on the flexible harness matches input 160 on the sensing membrane. Likewise ground 164 on the sensing membrane is connected to ground 252.

Figure 4:
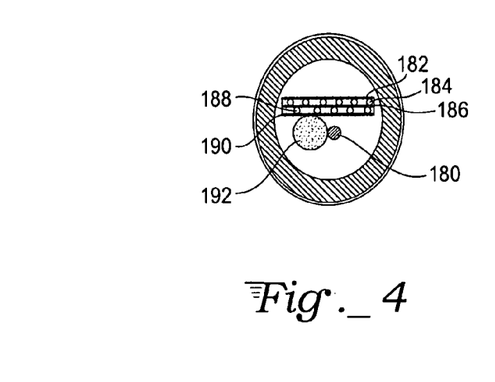
FIG. 4 is a cross-sectional view of a pressure sensor.

With reference to FIG. 4 a cross-section showing the internal cables of the system is illustrated. Axial stress bearing cable 180 extends through the interior of spool 126. Outer membrane 114 is disposed outside of spool 126. A flexible shielded cable also runs through the interior of spool 126. This cable is composed of an insulating layer 182, a first layer of conductive wires 184, a second insulating layer 186, a second layer of conductive wires 188, and a final outer layer of insulation 190. In some embodiments, an inner electrical ground layer, also separated on each side by insulation, may be used. In some embodiments an electrical ground layer lies above the first layer and below the final layer. This signal bearing ribbon provides a layer for input wires and a layer for output wires each of which are insulated both from wires in the same layer and wires in opposing layers. As shown in FIG. 6 these wires may be disposed in a signal bearing ribbon 181 that does not bear any substantial axial stress. This allows stable electrical connection of the wires to the pressure sensors 60, 62, 64. More specifically this allows connection to the pressure sensing membrane using the connection configuration shown in FIGS. 8A, 8B.

Figure 8C:
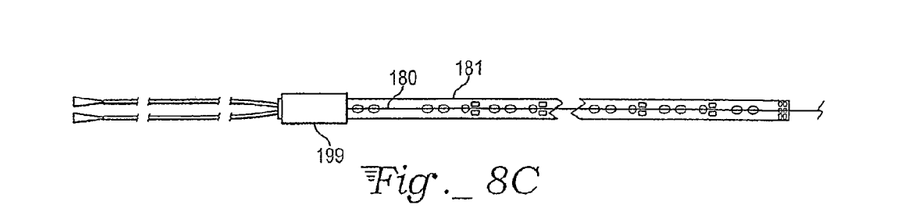
FIG. 8C is a top view of the flex harness and axial stress bearing cable ("leash").
Figures 8D, 8E:
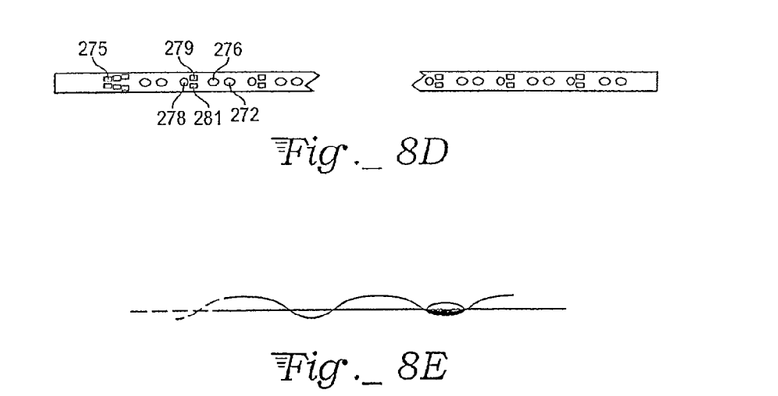
FIG. 8D is a top view of the flex harness.
FIG. 8E is a side view of the flex harness and leash.
Figure 9:
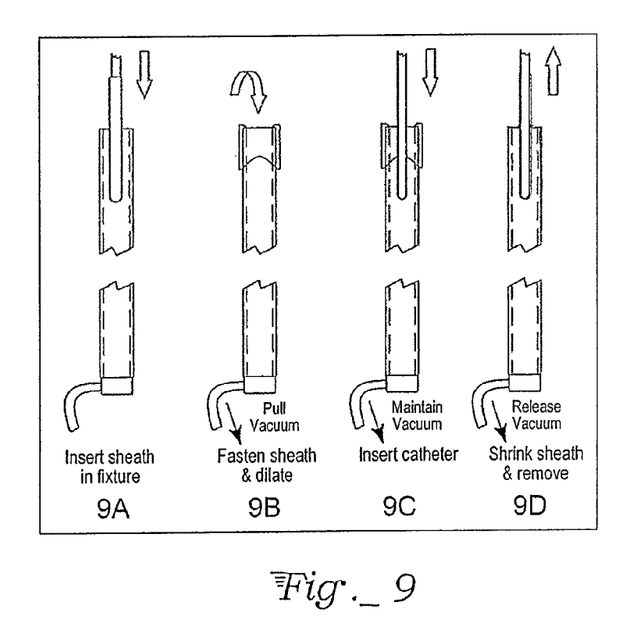
FIGS. 9A-9D are cross-sectional views showing the process of assembling an outer sheath on the pressure sensors.

In FIGS. 8C, 8D, 8E further details of the leash/axial support cable, flex harness and their connection is shown. In FIG. 8C, axial stress bearing cable is axially rigid, but flexible in bending to shunt axial loads from the rest of the assembly. Flex harness 181, contains the wires bringing the signal to and from the pressure sensors. At one terminus, the leash is bonded into a stainless steel relief tube 199. The flex harness 181 is also affixed to cable 180 in this tube as shown in FIG.

8E. This configuration acts to protect the solder connections of input and output wires to the flexing structure. The disclosed wire harness also makes the device easier to manufacture and assemble.

In FIG. 8D the flex harness is shown. At the proximal ends of the harness on each side are six pad solder patterns to allow connections of a total of twelve wires (e.g. the input or output wires) to the device. The three pad patterns 278, 279, 281 interconnect to the pads on the membrane as shown in FIGS. 8A, 8B. The holes 277, 276 allow the axial support cable to be threaded through the support harness.

Figure 7:
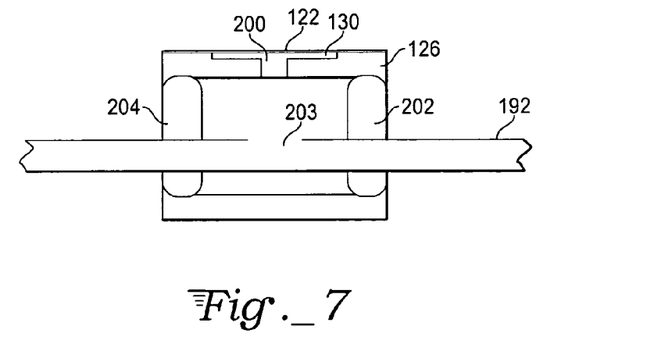
FIG. 7 is a side cross-section of an embodiment showing a venting design.

Also shown in FIG. 4 is vent tube 192. If a vented design is used it may be as shown in FIG. 7. As in the other embodiments a tubular structure 126 has an overlying pressure membrane 122. Between membrane 122 and a section of spool 126 is an air gap cavity 120 defined by nominally tubular pressure sensing membrane 122 and a metalized surface of spool 126. A vent hole 200 vents air gap 120 into a central space 201 within the interior spool 126. Also extending through the interior of spool 126 is vent tube 192 having an opening 203 to allow gas communication between air gap 120 and vent tube 192. Other pressure sensors are connected to the vent tube in a similar fashion with a block end of the tube at the distal end of the probe. At the proximal end of the probe, the vent tubes vent to room pressure or potentially a controlled pressure means such as a control pressure chamber or vacuum source. Also within spool 126 are cavity seals 202, 204. These seal the ends of spool 126 ensuring gas communication between air gap space 120 and vent tube 192. The primary role of these seals is to prevent the silicone that is injection molded between the sensors in subsequent operations, from entering the cavity inside the element and potentially blocking the vent tube or entering the air gap. As shown in FIG. 7 a single vent hole extends through spool 126. In other embodiments, a plurality of vent holes disposed through spool 126 at various locations of air gap 120 may be used.

The air gap sensors disclosed in the previous embodiments are capable of measuring pressure from a number of closely spaced locations along a sensitive length. This yields a high spatial resolution image of the region of interest. In esophageal measurements, separating sensors by 1.2 centimeters or less and having 32 sensors or more may be preferred as this allows detailed pressure profile mapping of the entire region of interest of most patients. In one embodiment a spacing of one centimeter and the use of 36 circumferential sensors is used.

Figure 5:
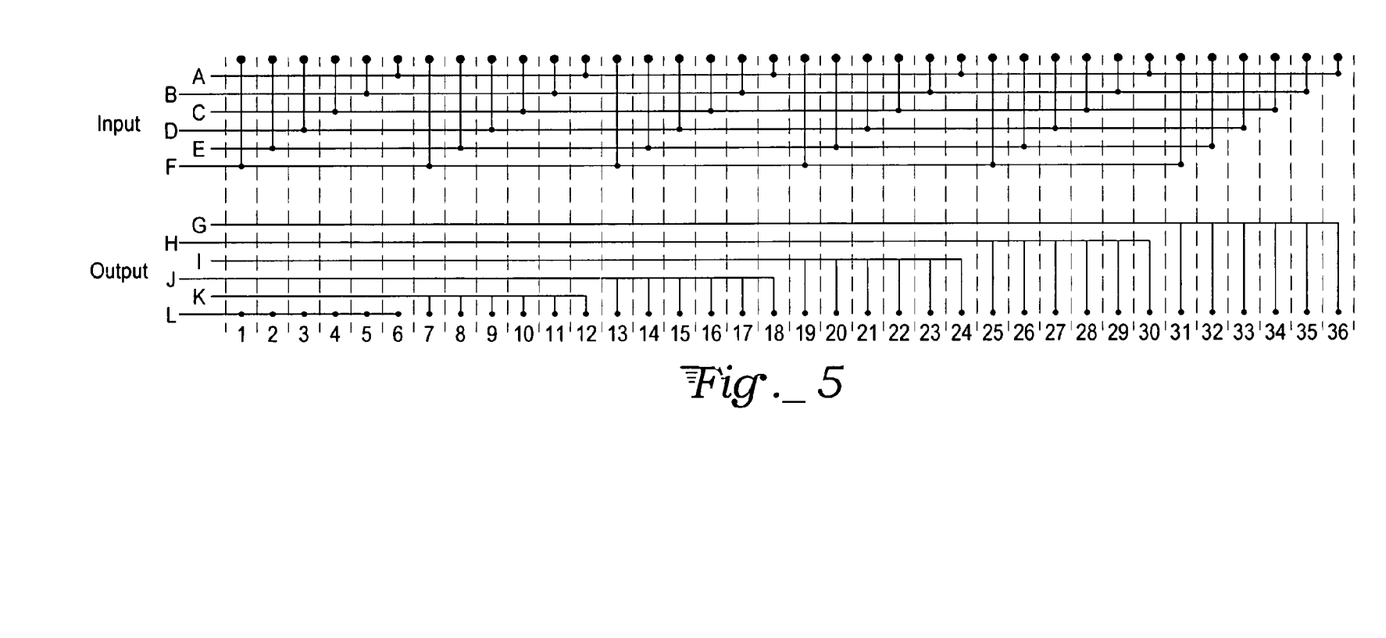
FIG. 5 is a multiplexed logic representation.

One important aspect of the present invention is the ability to use a relatively large number of sensors in a tube of relatively small dimensions. This allows the catheter to measure pressure from a spatial distribution while also providing a sufficiently small diameter to be tolerated by the patient during intubation and data collection. The reduction in the diameter is achieved in part through the use of a multiplex logic shown in FIG. 5. In FIG. 5 input wires A, B, C, D, E, and F and output wires G, H, I, J, K, and L are used with 36 sensors. For example input A provides an input to sensors 6, 12, 18, 24, 30 and 36. Similarly, wire B provides an input signal to sensors 5, 11, 17, 23, 29 and 35; wire C provides an input to sensors 4, 10, 16, 22, 28 and 34. Input wire D provides an input to sensors 3, 9, 15, 21, 27 and 33; wire E provides an input to sensors 2, 8, 14, 20, 26 and 32; and input wire F provides a signal to sensors 1, 7, 13, 19, 25, and 31.

Output wire L transmits the output from sensors 1-6, output wire K transmits the output from sensors 7-12, output wire J transmits the output from sensors 13-18, through 18, output wire I transmits the output signal from sensors 19-24, output wire H transmits the signal from sensors 25-30, and output wire G transmits the signal from sensors 31-36. The topology of the input and output may be as shown, may be reversed, or may be reconfigured in various manners. Any configuration in which more than one sensor shares an input or an output reduces the numbers of wires required. In the example of FIG. 5, six input wires and six output wires allow use of 36 sensors in a circumferential pressure sensing catheter which reduces the number of wires required on the signal bearing ribbon. This multiplex or group of sensors with matrix interconnections minimizes the number of electrical conductors required that run through the interior of the catheter.

In the preceding illustrated embodiments it should be realized that a number of the elements apply generally to pressure sensing probes. The illustrated method to multiplex a group of sensors with matrix interconnections that provide a bus to minimize the number of required electrical conductors in the body of the probe applies regardless of the number of input and output conductors used.

Each sensor has an input and an output. There are N inputs and M outputs to provide N×M unique addresses (i.e. support that many sensors uniquely). The required number of cable conductors is N+M, which is generally considerably less than N×M. In some embodiments the number of sensors sharing an input line and the number of sensors sharing an output line need not be the same. For the simplicity of the multiplex logic, symmetrical designs may be preferred. Those skilled in the art will realize that a number of alternative topologies may be designed. This matrix interconnection is adaptable to any pressure sensor in which a transducer converts the pressure signal to an electrical signal.

A second idea that applies generically to a variety of different pressure sensing probes is the use of the disclosed loosely routed signal cable in combination with a flexibly compliant, axially rigid cable for strain relief of the signal bearing component. This axially rigid cable makes the probe output much less sensitive to axial loads. Although the disclosed embodiment utilizes electrical signal as the signal means, it is envisioned that such a design would be adaptable to optical or electro-optical sensors as well.

Figure 13A:
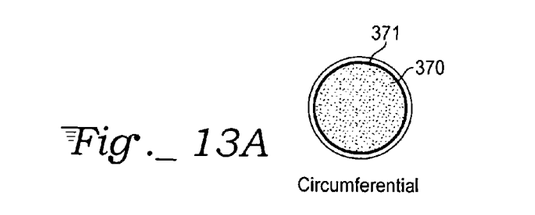
FIGS. 13A-13E are cross sectional views of a number of different embodiments of pressure sensors having various pressure sensing membrane positions or designs.
Figure 13B:
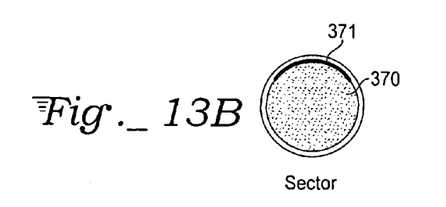
Figure 13C:
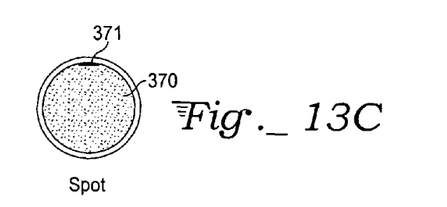
Figure 13D:
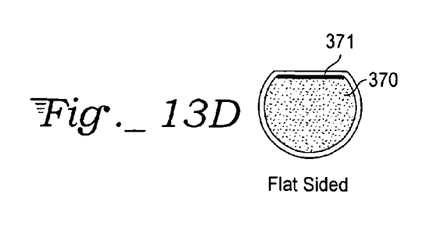
Figure 13E:
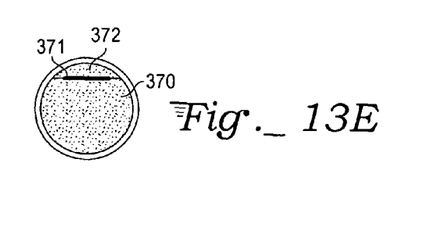

Those of skill in the art will understand that a number of different modifications and different embodiments may be made while still remaining in the scope of the invention. For example the pressure sensors may not be entirely circumferential. In each of FIGS. 13A-13E, the rigid internal component 370 supports a deformable sensing surface 371 separated from a rigid support surface by an air gap. The sensing membrane may by circumferential (as in FIG. 13A), a sector membrane (as in FIG. 13B), or a spot membrane (as in FIG. 13C). In addition the solid support may be flat sided, as in FIGS. 13D, 13E. In such instances, the sensing membrane may be positioned directly over a flat surface (as in FIG. 13D) or the sensor may be over lain with a low hysteresis medium that transmits pressure to a sensing membrane inside the outer sleeve and below media 372 (as shown in FIG. 13E).

The present design affords a number of advantages. A relatively large number of sensors (30 or more) may be accommodated in a compact design that allows for sensing over a biologically relevant length. The use of an axial stress bearing cable makes the device insensitive to positioning. The measurements from such a calibrated sensor are both repeatable and consistent. The catheter sterilization is rapid and simple. Because of rapid sterilization, there is less "down time" when the instrument would be unavailable because it is being cleaned. Because pressure measurements are made from the entire length of an organ, the diagnosis of disorders based on the pressure measurements from an entire organ are simplified.

Also, in some embodiments do not employ the axially rigid strain relief cable, the axial structure support for the assembly may be provided via a sufficiently rugged axial cable that also houses the electrical lines for input and output signal transmission.

In addition, the outer sleeve that extends the length of the assembly may be implemented as a piece-wise sleeve covering only one or more sensors, or the design, in absence of axial slits over the sensing membrane may have the membrane surface sealed such that the sensed pressure acts directly on the membrane without a permanent out sleeve. Additionally, there may be no permanent outer sleeve in any configuration of the membrane or sensor arrangement where the disposable sheath may be in contact directly with the sensors.

What is claimed is:

1. A pressure sensing catheter comprising:
   a plurality of pressure sensors, each comprising:
      a rigid inner tubular member having an electrically conductive layer defining an inner tubular electrode, the rigid inner tubular member further comprising a first annular raised structure and a second annular raised structure; and
      a deformable, outer tubular membrane comprising an electrically conductive layer formed on a dielectric polymer and defining an outer tubular electrode, the outer tubular electrode being attached to the first annular raised structure and the second annular raised structure such that the outer tubular electrode is spaced from the inner tubular electrode by an annular gap, said pressure sensors being disposed along the catheter, wherein each pressure sensor is configured to produce an electrical signal varying in response to the capacitance between the outer tubular electrode and the inner tubular electrode such that the electrical signal is representative of a circumferential pressure that is radially acting and distributed along a circumference of the sensor applied to the catheter tube at a location along the catheter;
   flexible material between pressure sensors of the plurality of pressure sensors; and
   a signal bus extending through the inner tubular member of each of the plurality of sensors and electrically connected to the electrically conductive layer of each outer tubular membrane and the inner tubular electrode of each pressure sensor, said signal bus extending to terminal connectors at a terminal end of said catheter, said terminal connectors configured to allow access to signals from said pressure sensors whereby a change in capacitance between the inner tubular electrode and the outer tubular electrode may be sensed.

2. The catheter of claim 1 wherein said pressure sensors provide output signals representative of a change in the annular gap caused principally by stretching of the tubular membrane in response to the circumferential pressure.

3. The catheter of claim 2 wherein:
   said electrically conductive layer of the deformable, outer tubular membrane comprises a metalized inner surface;
   the inner tubular member comprises a rigid metalized surface; and
   the gap separating the rigid metalized surface from said deformable membrane is an air gap.

4. The catheter of claim 1 wherein said signal bus comprises a first group of input lines and a second group of output lines.

5. The catheter of claim 4 wherein each input line of said first group of input lines is connected to a first terminal of a first plurality of the pressure transducers and each output line of said second group of output lines is connected to a second terminal of a second plurality of the pressure transducers.

6. The catheter of claim 5 wherein the input lines are configured to supply an A.C. signal voltage.

7. The catheter of claim 6 wherein said A.C. signal has a frequency below 250 kHz.

8. The catheter of claim 1 wherein said signal bus is carried in a ribbon cable.

9. The catheter of claim 1 further including a non-rigid outer tube.

10. The catheter of claim 9 wherein said non-rigid outer tube is 0.050 to 0.001 inch thick.

11. The catheter of claim 1 wherein the pressure sensors are spaced 1.2 cm or less center to center.

12. The catheter of claim 1 wherein the catheter has a longitudinal dimension and each tubular outer membrane has a plurality of longitudinal slits.

13. The catheter of claim 12, further comprising an outer sleeve over the plurality of longitudinal slits in each tubular outer membrane.

14. The pressure sensing catheter of claim 1, wherein the catheter has an elongated dimension and the plurality of pressure sensors comprises a linear array of pressure sensors numbering up to m×n disposed along the elongated dimension and the signal bus comprises m input lines, each of the m input lines connected to as many as n pressure sensors, and n output lines, each of the n output lines being connected to as many as m pressure sensors, m and n being positive integers.

15. The catheter of claim 14 wherein said plurality of pressure sensors includes 15 or more pressure sensors.

16. The catheter of claim 14 wherein the same number of sensors share an input line of the m input lines as share an output line of the n output lines.

17. The catheter of claim 15 wherein said pressure sensors are spaced 1.2 cm or less center to center.

18. The catheter of claim 14 wherein said signal bus comprises a ribbon cable comprising a first, second and third shield layers, wherein said input lines and said output lines are both disposed on layers of said ribbon wherein said input lines are disposed on an opposite side of said first shield layer from said output lines, said second shield layer is disposed between said input lines and an outside of said ribbon cable and said third shield layer is disposed between said output lines and the outside of ribbon cable.

19. The catheter of claim 18, wherein said ribbon cable further comprises shielding separating both the input lines and the output lines from an outside of said ribbon.

20. The catheter of claim 1, wherein said pressure sensors are attached to a support cable.

21. The catheter of claim 13, wherein said shielded ribbon cable includes a first insulating layer, a first layer of conductive wires, a second insulating layer, a second layer of conducting wires, and a third insulating layer.

22. The catheter of claim 1, wherein the signal bus comprises a flex harness.

23. The catheter of claim 1, wherein each of the plurality of pressure sensors further comprises a first adhesive member and a second adhesive member disposed between the deformable, outer tubular membrane and the first annular raised structure and the second annular raised structure, respectively, the first adhesive member and the second adhesive member securing the deformable, outer tubular membrane to the rigid inner tubular member.

24. The catheter of claim 1, wherein the outer tubular membrane is adapted to stretch in response to the circumferential pressure to change the capacitance between the inner tubular electrode and the outer tubular electrode.

25. The pressure sensing catheter of claim 1, wherein the rigid inner tubular member comprises a spool having the first and second annular raised structures.

26. A method of manufacturing a tubular capacitive pressure sensor, the pressure sensor comprising:
a pair of spaced apart, co-axially aligned surfaces comprising an outer deformable, electrically conductive membrane having a tubular structure around an inner axially aligned non-deformable support structure having an electrically conductive surface separated from the deformable membrane by a gap having a characteristic gap dimension; and
electrical signal leads positioned proximate to said membrane surface, making separate contact with the deformable conductive membrane surface and the non-deformable conductive surface, adapted for coupling to a signal source having a frequency to measure capacitive impedance across the electrical signal leads, wherein the capacitive impedance varies as circumferential pressure that is radially acting and distributed along a circumference of the sensor changes the dimension of the gap, and the method comprising:
rolling the deformable, electrically conductive membrane into the tubular structure; and
attaching the deformable, electrically conductive membrane around the circumference of the tubular structure at a first location and a second location, with the electrically conductive membrane separated from the tubular structure between the first location and the second location to form the gap.

27. The method of manufacturing the sensor of claim 26 wherein the support structure comprises a spool and said inner surface is a surface on the spool, said spool having annular raised structures and the annular raised structures are positioned in the first location and the second location.

28. The method of manufacturing the sensor of claim 27 wherein said electrically conductive membrane is comprised of a polyimide membrane having a patterned conductive area.

29. The method of manufacturing the sensor of claim 28 wherein the electrical signal leads are positioned on an arm that extends from a side of the membrane.

30. The method of manufacturing the a sensor of claim 26 wherein the deformable outer membrane has a plurality of longitudinal slits.

31. The method of manufacturing the sensor of claim 29 further including a ground on said sensor, said ground electrically joined to said spool through a trace on the arm.

32. The method of manufacturing the sensor of claim 26, wherein:
the deformable, electrically conductive membrane comprises a first member and the non-deformable electrically conductive surface comprises a second member; and
the tubular capacitive pressure sensor further comprises adhesive members securing the first member to the second member.

33. The method of manufacturing a tubular capacitive pressure sensor of claim 26, wherein the inner non-deformable support structure comprises a probe.

34. The method of manufacturing a tubular capacitive pressure sensor of claim 26, wherein the inner non-deformable support structure is coupled to a flexible material to form a flexible catheter.

35. A method of operating a capacitive pressure sensor, the capacitive pressure sensor comprising:
a cylindrical outer sensing membrane comprising a flexible dielectric member with a metallic coating on an inner surface forming a first electrode, said sensing membrane having a plurality of slits through the flexible dielectric member and the metallic coating defining a plurality of elongated conductive regions in a first portion of the metallic coating, each elongated conductive region being disposed between adjacent slits of the plurality of slits, the metallic coating having a second portion interconnecting elongated conductive regions of the plurality of elongated conductive regions;
a cylindrical inner rigid structure having at least two spacer elements creating an inner air gap between said outer sensing membrane and an underlying metallic layer on said inner rigid structure, said underlying metallic layer forming a second electrode;
a first conductive trace, the first conductive trace coupling the first electrode to a first contact terminal; and
a second conductive trace, the second conductive trace allowing connection to the second electrode; and
the method comprising:
providing a voltage between the first electrode and the second electrode;
exposing the sensor to a circumferential pressure that is radially acting and distributed along a circumference of the sensor from outside of the cylindrical outer sensing membrane;
deforming, under the circumferential pressure, the flexible dielectric member towards the cylindrical inner structure; and
sensing a change in capacitance between the plurality of elongated conductive regions defined by the plurality of slits in the metallic coating of the first electrode and the second electrode to measure the circumferential pressure.

36. The method of operating a capacitive pressure sensor of claim 35, wherein the cylindrical inner rigid structure comprises a probe.

37. The method of operating a capacitive pressure sensor of claim 35, wherein the cylindrical inner rigid structure is coupled to a flexible material to form a flexible catheter.

* * * * *